(12) United States Patent
Chu et al.

(10) Patent No.: US 7,279,340 B2
(45) Date of Patent: Oct. 9, 2007

(54) SYNTHESIS AND APPLICATION OF PROCAINAMIDE ANALOGS FOR USE IN AN IMMUNOASSAY

(75) Inventors: Victor P. Chu, Hockessin, DE (US); Zhu Teng, Boothwyn, PA (US); Steve P. A. Goss, Wilmington, DE (US); Ronald L. Edwards, Bear, DE (US); Kelle M. Garvey, Wilmington, DE (US); Timothy J. Gorzynski, Neward, DE (US); William D. Bedzyk, Odessa, DE (US)

(73) Assignee: Dade Behring Inc., Deerfield, IL (US)

( * ) Notice: Subject to any disclaimer, the term of this patent is extended or adjusted under 35 U.S.C. 154(b) by 575 days.

(21) Appl. No.: 10/819,831

(22) Filed: Apr. 7, 2004

(65) Prior Publication Data

US 2005/0227288 A1 Oct. 13, 2005

(51) Int. Cl.
  *G01N 33/546* (2006.01)
  *G01N 33/543* (2006.01)
  *C07C 237/28* (2006.01)
  *G01N 37/00* (2006.01)
(52) U.S. Cl. .................. 436/533; 436/523; 436/56; 436/815; 568/306; 564/123
(58) Field of Classification Search ............... 436/523, 436/533, 56, 815; 568/306; 564/123
  See application file for complete search history.

(56) References Cited

U.S. PATENT DOCUMENTS

| 5,439,798 | A | | 8/1995 | Sigler et al. ............... 435/7.7 |
| 5,525,474 | A | | 6/1996 | Sigler et al. ............... 435/7.7 |
| 5,747,352 | A | | 5/1998 | Yan et al. .................. 436/533 |
| 5,876,727 | A | | 3/1999 | Swain et al. .............. 424/193.1 |
| 5,981,296 | A | * | 11/1999 | Stout ......................... 436/501 |
| 6,159,698 | A | | 12/2000 | Staples et al. ............. 435/7.1 |
| 6,319,674 | B1 | | 11/2001 | Fulcrand et al. ........... 435/7.1 |
| 6,455,288 | B1 | | 9/2002 | Jakobovits et al. ......... 435/190 |
| 6,524,808 | B1 | | 2/2003 | Dorn et al. ................. 435/26 |
| 6,696,304 | B1 | | 2/2004 | Davies ....................... 436/518 |
| 6,743,585 | B2 | | 6/2004 | Dellinger et al. ............. 435/6 |

FOREIGN PATENT DOCUMENTS

EP 199042 A1 * 10/1986

* cited by examiner

*Primary Examiner*—Long V. Le
*Assistant Examiner*—Shafiqul Haq
(74) *Attorney, Agent, or Firm*—Cynthia G. Tymeson

(57) ABSTRACT

The present invention relates to immobilized procainamide analogs, as well as to a method of making immobilized procainamide analogs. These immobilized analogs are prepared by activating the carboxyl group on a substituted p-benzoic acid derivative toward nucleophilic attack; reacting the activated benzoic acid derivative with a polyamine to produce the benzoic acid derivative of Formula 3:

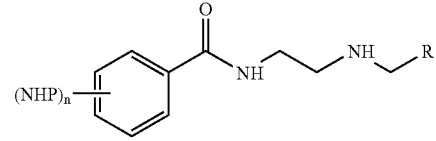

Formula 3 and binding the benzoic acid derivative of Formula 3 to a latex polymer having functional groups that react with aliphatic amino groups. A method of conducting an immunoassay using the immobilized procainamide analog Formula 3 is described, comprising the steps of preparing a solution comprising said immobilized procainamide analog; adding a sample suspected of containing procainamide to said solution; adding an anti-procainamide antibody to said solution and observing the rate of increase in solution turbidity following antibody addition.

2 Claims, 3 Drawing Sheets

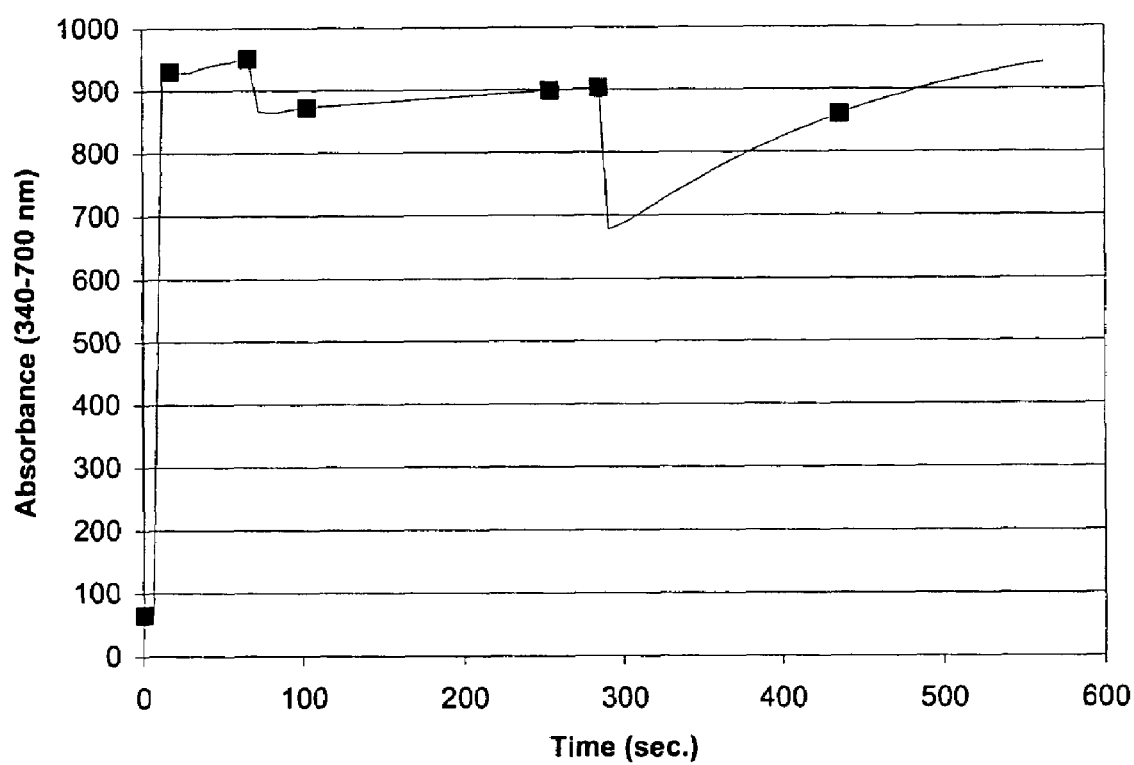
Fig. 1: Absorbance as a Function of Time in a PETINIA Assay

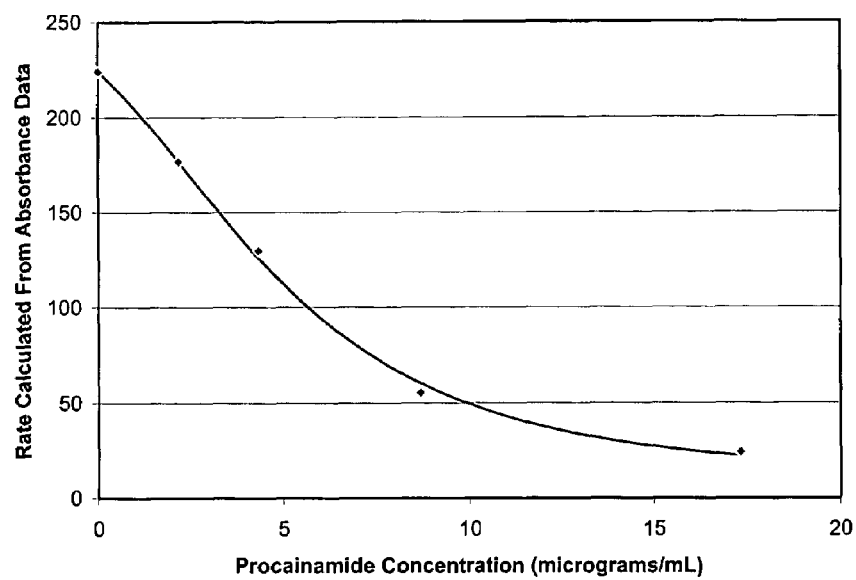

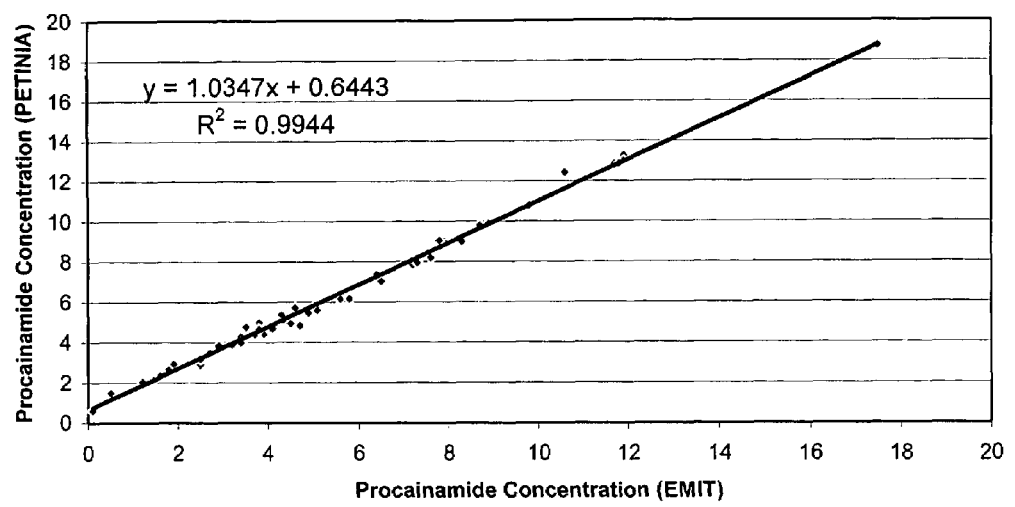

SYNTHESIS AND APPLICATION OF PROCAINAMIDE ANALOGS FOR USE IN AN IMMUNOASSAY

FIELD OF THE INVENTION

The present invention relates to novel derivatives of procainamide. The derivatives may be used as immunogens to stimulate antibody production, or to produce particulate polymer conjugates useful in immunoassays for detection of procainamide. Also provided are methods for synthesis of the procainamide derivatives and their polymer conjugates.

BACKGROUND OF THE INVENTION

The ability to assess whether an individual has been exposed to a pharmacological agent, and a capability of determining the concentration of such an agent in a biological sample is of broad importance in medicine, law enforcement and other areas. In particular, the narrow window of therapeutic utility, and the proximity of that window to toxicity for many drugs such as Procainamide have necessitated the development of assays capable of detecting and quantifying such substances.

Procainamide is a pharmaceutical agent having utility in treatment of irregular heartbeats. It functions to restore the heartbeat to a normal rhythm and to slow an overactive heart, thereby allowing the heart to work more efficiently. Procainamide produces its beneficial effects by slowing nerve impulses in the heart and reducing sensitivity of heart tissues. It is important to monitor procainamide levels to ensure that a patient is receiving the correct dose. This is particularly important with procainamide, as monitoring helps avoid such side effects of procainamide overdose as fast and irregular heartbeat, confusion, stupor, decreased blood pressure, fainting, and cardiac arrest. A reliable test for procainamide in the blood also is useful for assisting medical personnel in the diagnosis of the cause of less common procainamide-induced neurological side effects such as hallucinations, depression, and psychosis.

Immunoassays are assay systems that exploit the ability of an antibody to specifically recognize and bind to a particular target molecule, and operate by incubating an antibody that is capable of binding to a predetermined analyte molecule with a sample that is suspected of containing analyte. The concentration of the target molecule is proportional to the concentration of antibody-analyte immune complexes. In some immunoassays, the antibody is bound to a support. Free target molecule is allowed to react with the support, and the concentration of the target molecule is determined by measuring the concentration of antibody-analyte complex immobilized to the support.

Target molecules that have become bound to the immobilized antibody can be detected through the use of a labeled, second antibody that is capable of binding to a second binding site on the target molecule (i.e., a "sandwich" immunoassay). Immobilization of the labeled antibody on the support is proportional to the concentration of the target in the sample. Alternatively, in a competitive assay, the sample is incubated with a known amount of labeled target and an immobilized antibody. The target molecules in the sample compete with the labeled target molecules for the antibody binding sites. Thus, the concentration of antibody-bound labeled target molecules is inversely proportional to the concentration of target molecule in the sample.

The utility of an immunoassay in detecting an analyte depends upon its capacity to report the extent of the formation of immune complexes between the antibody employed and the analyte whose presence or concentration is being measured. In general, two independent approaches exist for increasing this capacity. The first approach involves labeling one or more of the reagents.

Another approach involves increasing the size of the immune complex to the point where it becomes capable of scattering light. In such cases, agglutination or turbidimetric immunoassay methods may be employed. Turbidimetric methods measure the reduction of light transmitted through the suspension of particles or aggregates. The reduction is caused by reflection, scatter, and absorption of the light by the aggregates. In turbidimetric assays, the rate of change in light scatter may also be measured, and provides an indication of the amount of antigen present.

Turbidimetric assays for therapeutic drugs and drugs of abuse which use hapten coated particles are commercially available. An example of such an assay is a particle-enhanced turbidimetric-inhibition immunoassay (PETINIA). This immunoassay format uses drug-hydrophilic linker-particle reporter reagents (particle reagents). These particle reagents utilize very small latex particles (e.g., 70 nm) to which have been attached a drug or other compound of interest. When viewed with monochromatic light having a wavelength (e.g., 340 nm) larger than the diameter of the suspended particles, e.g., the suspension is relatively transparent. Under optimal conditions, addition of antibody specific for the drug on the particles will cause the particles to agglutinate, forming insoluble complexes. These complexes cause the suspension to become turbid and scatter light. When an antibody is added to a sample containing drug/particle conjugates and free drug, free drug competes with particle-bound drug for antibody, thereby inhibiting both the rate and extent of agglutination. This provides the basis for quantifying the amount of drug in the sample. Specifically, in the present invention, procainamide analog-hydrophilic spacer-particle reagents and anti-procainamide antibodies enable a rapid, precise and accurate PETINIA method for determining the amount of procainamide present in biological fluids. Such methods, by enhancing both the rate of immune complex formation, and the size of the immune complex, provide more efficient and effective immunoassays for determining the concentration of medically important pharmacological agents, such as procainamide. The present invention provides reagents and methods for conducting such improved immunoassays.

It is an object of the invention to provide novel procainamide analogs having a linking group that may be used to immobilize them to a support, in particular polymeric support. It is another object of the invention to provide novel methods of synthesizing biologically active procainamide analogs from aminobenzoic acids. It is also an object of the invention to provide particulate procainamide analog/polymer conjugates that may be used to detect the presence of procainamide antibodies. It is a further object of the invention to provide an immunoassay for procainamide which functions by measuring changes in the turbidity of a solution or dispersion containing a known quantity of a particulate procainamide analog/polymer conjugate, a known quantity of a procainamide antibody, and a sample suspected to contain procainamide.

The foregoing objects and advantages of the invention are illustrative of those that can be achieved by the present invention and are not intended to be exhaustive or limiting of the possible advantages which can be realized. Thus, these and other objects and advantages of the invention will be apparent from the description herein or can be learned from practicing the invention, both as embodied herein or as modified in view of any variation which may be apparent to those skilled in the art. Accordingly, the present invention resides in the novel methods, arrangements, combinations and improvements herein shown and described.

SUMMARY OF THE INVENTION

In light of the present need for procainamide-based assays, a brief summary of the present invention is presented. Some simplifications and omission may be made in the following summary, which is intended to highlight and introduce some aspects of the present invention, but not to limit its scope. Detailed descriptions of a preferred exemplary embodiment adequate to allow those of ordinary skill in the art to make and use the invention concepts will follow in later sections.

In one embodiment, the present invention relates to procainamide analogs of Formula 3:

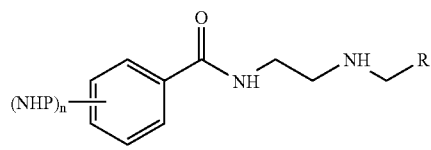

Formula 3 where each P is a protecting group, an alkyl group, an acyl group, or a hydrogen atom; R is hydrogen or lower alkyl; and n is 1, 2, or 3. The invention further relates to a method of making procainamide analogs by activating the carboxyl group on a substituted benzoic acid derivative of Formula 1:

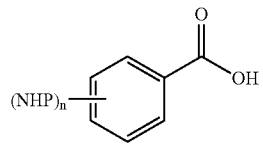

Formula 1 toward nucleophilic attack. The activated benzoic acid derivative is then reacted with a polyamine of Formula 2,

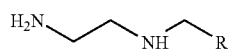

Formula 2 to produce a benzoic acid derivative of Formula 3. The analogues of Formula 3 may then be reacted with a compound of Formula 4:

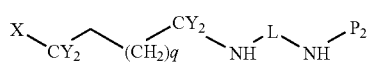

Formula 4 where X is a leaving group; each $CY_2$ group is a methylene group, an alkylmethylene group, or a carbonyl group; L is an alkylene group having from 2 to 10 carbons or a group of the Formula $(CH_2CH_2O)_pCH_2CH_2$, where p is between 1 and 4; and $P_2$ is a protecting group. The result is an analog of Formula 5:

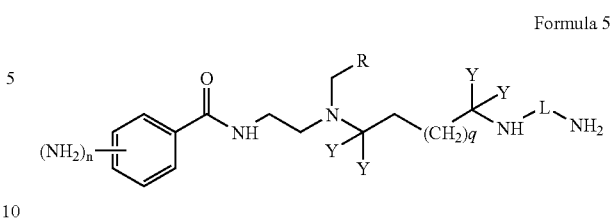

Formula 5

In another embodiment, the present invention relates to immobilized procainamide analogs, as well as to a method of making immobilized procainamide analogs. These immobilized analogs are prepared by activating the carboxyl group on the substituted benzoic acid derivative of Formula 1 toward nucleophilic attack; reacting the activated benzoic acid derivative with the polyamine of Formula 2 to produce the benzoic acid derivative of Formula 3; and binding the benzoic acid derivative of Formula 3 to a latex polymer having functional groups that react with aliphatic amino groups, producing an immobilized procainamide analog of Formula 3a:

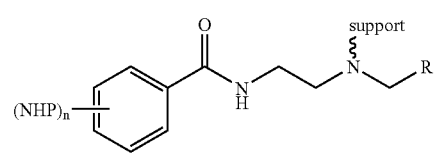

Formula 3a where polymer bound to the procainamide moiety by the wavy line is a support; in a particular embodiment, a latex polymer particle, which is bound either directly or indirectly to procainamide.

In a third embodiment, a method of conducting an immunoassay using the immobilized procainamide analogue Formula 3a is described, comprising the steps of preparing a solution comprising said immobilized procainamide analog; adding a sample suspected of containing procainamide to said solution; adding an anti-procainamide antibody to said solution; and monitoring the rate of the increase in the solutions turbidity. Further, the method may include a step of observing any changes in solution turbidity following sample addition to rule out sample-induced agglutination.

DESCRIPTION OF THE DRAWINGS

In order to better understand the present invention, reference is made to the accompanying drawings, wherein:

FIG. 1 shows a plot of kinetics of the increase in absorbance versus time for PETINIA assays with representative data in Table 1.

FIG. 2 shows a standard curve for a PETINIA assay, derived from the data in Table 2.

FIG. 3 shows a correlation of the concentration data derived from an EMIT® assay to the concentration data derived from a PETINIA assay.

DESCRIPTION OF THE PREFERRED EMBODIMENTS (1) Procainamide Analogs

Procainamide analogs which may be immobilized to a polymeric support have great potential in assays for procainamide in biological fluids. Varieties of such analogs have been prepared, and will be described herein.

A first procainamide analog is 4-amino-N-(2-ethylamino-ethyl)benzamide, Formula 6:

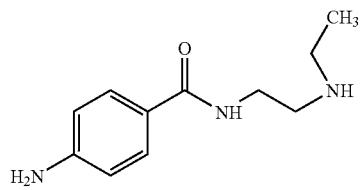

Formula 6

This compound may be prepared from p-aminobenzoic acid, Formula 7, in accordance with Scheme I. According to this procedure, the amino group on p-aminobenzoic acid is protected by reacting the acid with a carbonic acid diester, giving an N-alkoxycarbonyl derivative of p-aminobenzoic acid. di-t-butyl dicarbonate is a particularly useful diester, producing the protected aminobenzoic acid, Formula 8. The carbonyl group is then activated toward nucleophilic attack with N,N-disuccinimidyl carbonate, producing Formula 9, which may or may not be isolated. This compound is then reacted with N-ethylethylenediamine to produce compound 10. Alternatively, protected compound 8 may be directly converted into an amide, Formula 10, by reaction with N-ethylethylenediamine in the presence of dicyclohexyl carbodiimide (DCC). After preparation of Formula 10, the protecting group may be removed by treatment with acid, generating Formula 6.

More broadly, this process may be used to synthesize a variety of amides of Formula 11:

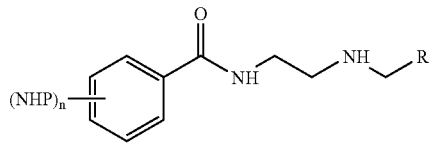

Formula 11 where R is hydrogen, alkyl having from 1 to 10 carbons, cycloalkyl, or an aromatic ring; and n is 1, 2, or 3. This is done by reacting Formula 12:

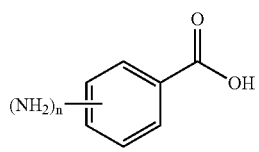

Formula 12 with one equivalent of di-t-butyl dicarbonate for each amino group, producing a protected acid of Formula 1, where P is a t-butoxycarbonyl group. The protected benzoic acid derivative is activated with DSC, and is then reacted with a polyamine of Formula 2:

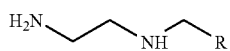

Formula 2 where R is hydrogen, alkyl having from 1 to 10 carbon atoms, or aryl, to produce a benzoic acid derivative of Formula 3. The t-butoxycarbonyl protecting groups may be removed by treating Formula 3 with trifluoroacetic acid.

SCHEME 1

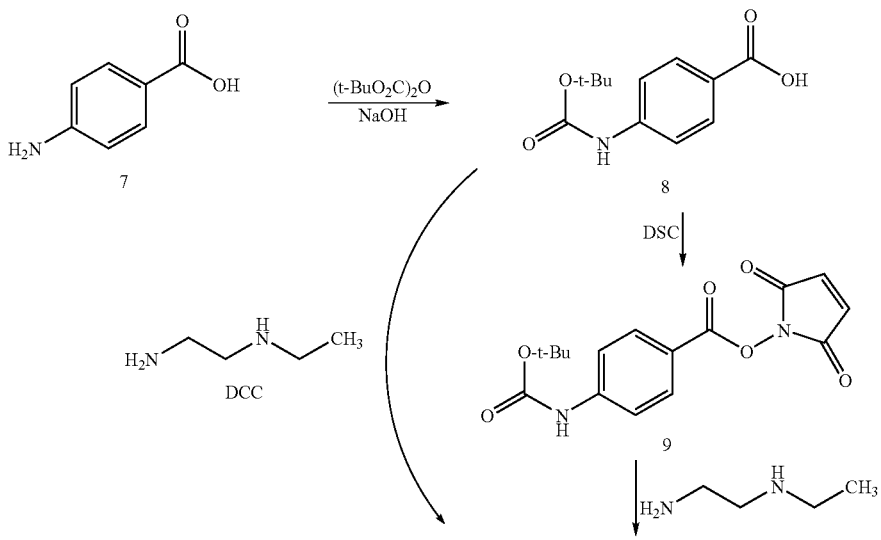

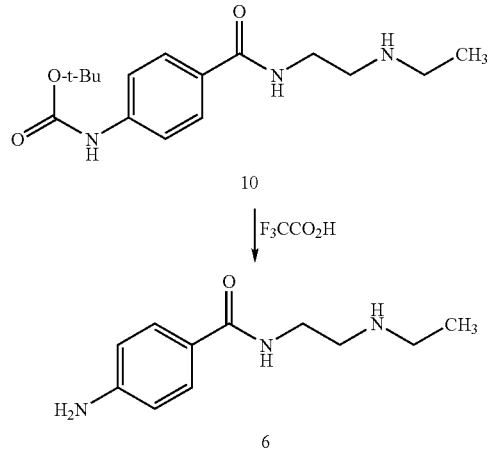

10

More elaborate procainamide analogs having long-chain substituents may also be prepared. The analogues of Formula 3 may be reacted with a compound of Formula 4:

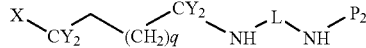

Formula 4 where X is a leaving group; each $CY_2$ group is a methylene group, an alkylmethylene group, or a carbonyl group; L is an alkylene group having from 2 to 10 carbons or a group of the Formula $(CH_2CH_2O)_pCH_2CH_2$, where p is between 1 and 4; and $P_2$ is a protecting group. The result is an analog of Formula 5:

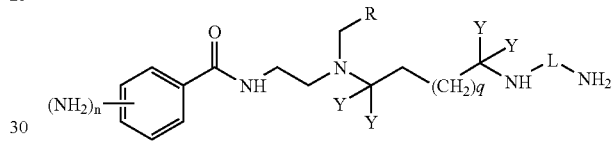

Formula 5

Particularly preferred compounds of Formula 4 include haloamides of Formula 13:

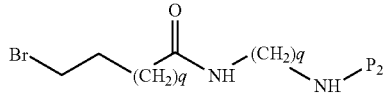

Formula 13

Formula 13 may be obtained by reacting an ω-bromoalkanoic acid (for example, 5-bromopentanoic acid), Formula 14, with an activating agent such as N,N-disuccinimidyl carbonate to produce an activated carboxylic ester. The activated ester is then reacted with a protected diamine to produce a haloamide, Formula 15 (See Scheme 2).

SCHEME 2

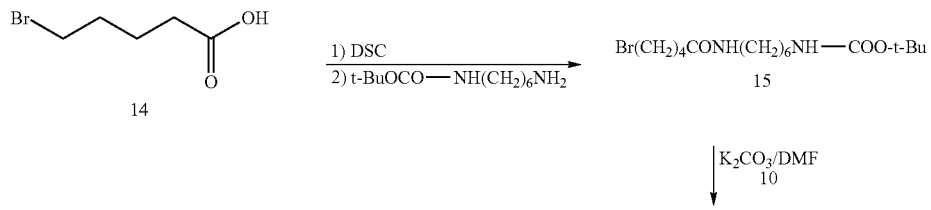

-continued

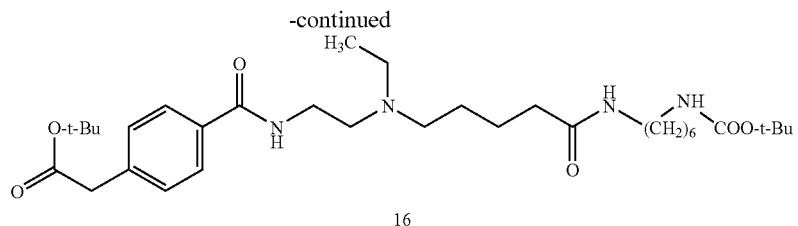

16

Formula 10 is then reacted with Formula 15 to produce a protected long-chain benzamide, Formula 16.

Similarly, a protected diamine of Formula 17:

Formula 17

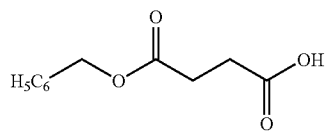

may be reacted with a protected acid ester of Formula 18:

Formula 18 to produce an amidoester of Formula 19:

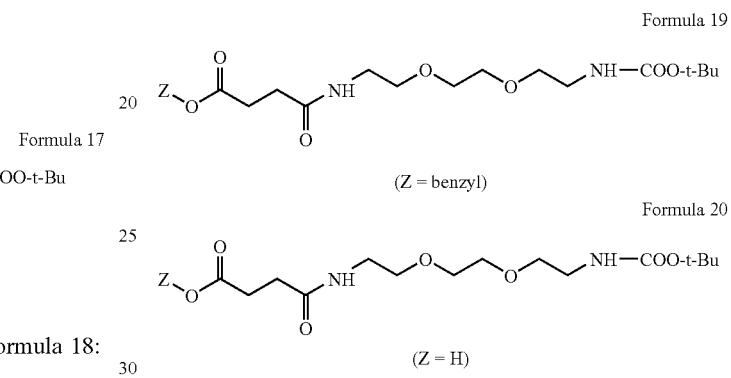

Alternatively, Formula 18 may be activated by reacting the acid with N,N-disuccinimidyl carbonate, and then the activated compound may be reacted with Formula 17 to produce Formula 19.

The benzyl group on Formula 19 may then be removed by hydrogenolysis to produce an amidoacid, Formula 20, which can then be reacted with procainamide Formula 10 in the presence of dicyclohexylcarbodiimide or N,N-disuccinimidyl carbonate, giving a procainamide analog of Formula 21:

21

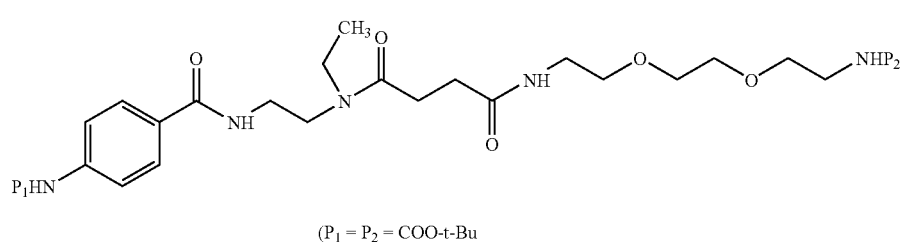

($P_1 = P_2 = $ COO-t-Bu)

-continued

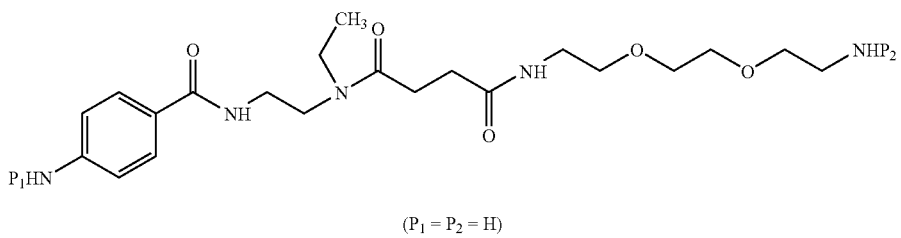

22

$(P_1 = P_2 = H)$

The t-butoxycarbonyl protecting groups on the nitrogen atoms may then be removed with trifluoroacetic acid to produce procainamide analog, Formula 22.

SYNTHESIS EXAMPLE 1

Preparation of Formula 22

(A) Preparation of Protected p-Aminobenzoic Acid

Protected p-aminobenzoic acid was prepared by dissolving 24 g (0.17 mol) p-amino-benzoic acid and 11.5 g (0.288 mol) sodium hydroxide in 300 ml water. Di-t-butyl dicarbonate (42 g; 0.193 mol) was added to the solution, but failed to dissolve, giving a nonhomogeneous mixture. Tetrahydrofuran (300 ml) and methanol (150 ml) were added to the mixture, the solids dissolved and a homogeneous solution was obtained. The solution was stirred for 5.5 hours while monitoring pH, with 5.5 g NaOH added to the solution after the pH dropped to about 7.0. The organic solvents were removed from the reaction mixture with a rotary evaporator, and the remaining aqueous solution was poured into 1000 ml water and acidified with 75 ml 6 N HCl to a pH of between 3 and 4 with mechanical stirring. The white solid, which precipitated, was recovered by filtration and dried in an oven under high vacuum. The dried solid, identified as the t-butyl carbamate, Formula 8, was obtained in a yield of 28.11 g (68%).

(B) Activation of Protected p-Aminobenzoic Acid

The t-butyl carbamate of p-aminobenzoic acid (9.48 g; 40 mmol) and N,N'-disuccinimidyl carbonate (11.26 g; 44 mmol) were combined with 14 ml triethylamine in 200 ml tetrahydrofuran (THF). The reaction mixture was stirred under a nitrogen atmosphere at room temperature for three hours. Thin layer chromatography (TLC) was then performed using a solvent mixture of 50% hexane and 50% ethyl acetate to confirm that the reaction had reached completion. The reaction mixture was next added to 100 ml of a saturated aqueous $NaHCO_3$ solution, and extracted three times with 250 ml ethyl acetate. The organic extracts were combined, and dried over anhydrous sodium sulfate. The solvent was removed in a rotary evaporator, and the solid residue was dissolved in a mixture of 40 ml ethyl acetate and 60 ml hexane. The solution was allowed to stand overnight at room temperature, and a solid material recrystallized from the solution. This product, identified as activated ester, Formula 9, was isolated in a yield of 10.3 g (77%).

(C) Preparation of Formula 10

Activated ester, Formula 9 (1.077 g; 3.22 mmol), was dissolved in 6 ml dichloromethane (DCM). The solution of Formula 9 was then added drop-wise to a room temperature solution of N-ethylethylenediamine (0.284 g; 3.22 mmol) in DCM under a nitrogen atmosphere. The reaction mixture was stirred for 5.5 hours. Dichloromethane (100 ml) was then added to the reaction mixture, and the resulting solution was extracted with a saturated aqueous solution of sodium bicarbonate (20 ml). The organic phase was separated from the aqueous phase and dried over sodium sulfate. The solvent was then evaporated, leaving a solid residue identified as Formula 10.

(D) Preparation of Protected Procainamide Analog, Formula 21

Amidoacid, Formula 20 (520 mg; 1.494 mmol), N,N-disuccinimidyl carbonate (383 mg; 1.494 mmol), and 0.2 ml triethylamine were stirred at room temperature under a nitrogen atmosphere in a solution of 5 ml THF for 2 hours. Benzamide, Formula 10, (458.6 mg; 1.494 mmol) was then added drop-wise to the THF solution, and the reaction mixture was allowed to stir overnight. The THF solvent was then evaporated under vacuum using a rotary evaporator. Methylene chloride (100 ml) was then added to the residue, and the resulting solution was washed twice with 10 ml deionized water. The organic phase was then dried over sodium sulfate, and the solvent was removed. The resulting crude product was purified by column chromatography. The purified protected procainamide analog, Formula 21, was isolated in an amount of 570 mg (60%).

(E) Preparation of Procainamide Analog, Formula 22

Protected procainamide analog, Formula 21 (570 mg; 0.895 mmol), and 4 ml of a 40% solution of trifluoroacetic acid in dichloromethane were stirred at room temperature overnight. The solvent was then evaporated from the reaction mixture. The residue was purified by column chromatography using methanol as a diluent. A product identified as Formula 22 was isolated in a yield of 247.7 mg (64%).

(2) Use of Procainamide Analogs in Assays

The procainamide analogs of the current invention bind selectively to antibodies generated against procainamide. This allows the analogs to be used to indirectly or directly detect the presence of procainamide in biological fluids. Thus, the present invention provides a powerful tool for monitoring of procainamide levels.

The current invention may be used in a variety of test methods. For example, the inventive procainamide analogs may be immobilized onto a test strip, such as a microwell test strip, a glass slide or other support. One such method would involve derivatization of glass slides having 3-aminopropyl-triethoxysilane-coated glass slides. 5-bromopentanoic acid is then activated with disuccinimidyl carbonate, and the amino-functionalized plated is allowed to react with the functionalized acid. The result is a plate having exposed bromoalkyl groups. This plate may then be reacted with the t-butyl carbamate of p-amino-N-(ethylamino)ethyl-benzamide, Formula 6, in order to bind procainamide analog, Formula 6, to the plate through a long-chain linking group.

A linking group is a portion of a structure which connects 2 or more substructures. A linking group has at least 1 uninterrupted chain of atoms extending between the substructures. The atoms of a linking group are themselves connected by chemical bonds. The number of atoms in a linking group is determined by counting the atoms other than hydrogen. A linking group typically comprises about 2 to about 15 atoms and may comprise a chain of from 2 to 8 atoms, each independently selected from the group normally consisting of carbon, oxygen, sulfur, nitrogen, halogen and phosphorous. Where the linking group provides attachment of a protein to the hydroxyl group of the benzene ring, the linking group usually comprises at least 5 atoms or, when less than 5 atoms, the linking group does not comprise solely carbon atoms or oxygen atoms. For the most part, when a linking group has a non-oxocarbonyl group including nitrogen and sulfur analogs, a phosphate group, an amino group, alkylating agent such as halo or tosylalkyl, oxy (hydroxyl or the sulfur analog, mercapto) oxocarbonyl (e.g., aldehyde or ketone), or active olefin such as a vinyl sulfone or α-, β-unsaturated ester, these functionalities will be linked to amine groups, carboxyl groups, active olefins, alkylating agents, e.g., bromoacetyl. Where an amine and carboxylic acid or its nitrogen derivative or phosphoric acid is linked, amides, amidines and phosphoramides will be formed. Where mercaptan and activated olefin are linked, thioethers will be formed. Where a mercaptan and an alkylating agent are linked, thioethers will be formed. Where aldehyde and an amine are linked under reducing conditions, an alkylamine will be formed. Where a carboxylic acid or phosphate acid and an alcohol are linked, esters will be formed. Various linking agents are well known in the art; see, for example, Cautrecasas, *J. Biol. Chem.* (1970) 245:3059.

The plate having procainamide analog Formula 6 immobilized thereto may be used within conventional immunoassays to detect the presence and/or concentration of procainamide in a variety of assays.

The inventive analogs may also be used in Particle Enhanced Turbidometric Inhibition Immunoassays (PE-TINIA).

PETINIA is an assay format that utilizes latex particle-analyte conjugates, such as those described above, in order to determine analyte concentrations in solution. PETINIA reactions are composed of three components:

1) latex particles to which an antigen or an antigen analogue has been attached;
2) antibodies generated to recognize the antigen; and
3) an assay buffer.

Non-specific agglutination (agglutination in the absence of antibody) of the latex-antigen conjugates is thought to be prevented due to electrostatic repulsion between similarly-charged conjugates, and steric repulsion of bound surface components (the antigens or antigen analogues). Upon reaction of these groups with antibodies, the charge of the latex-bound moieties is altered, resulting in the formation of insoluble complexes. Accumulation of these complexes in the reaction solution will increase the amount of light scattered when the reaction chamber is illuminated, the extent of which can be monitored by turbidimetry. The assay buffer used in this reaction must be optimized to prevent non-specific reactions from occurring, which may affect particle stability. The buffer is optimized in order to manage the shape of the calibration curve and determine the concentration range of analyte detection.

When a sample containing free antigen (also referred to as an analyte) is present in the reaction solution, competition for the antibody occurs between the bound antigen or antigen analogue in the particle conjugate and the analyte. This results in an inhibition of the formation of insoluble complexes and therefore an inhibition of the increase in turbidity. This inhibition can be calibrated by addition of known concentrations of analyte, enabling determination of analyte concentration in various samples.

In most immunoassays, any cross-reactivity of metabolites of the analyte and any additional compounds that may be present in the sample populations should be understood, and if necessary, accounted for in order to ensure that the result obtained is reflective of the true analyte concentration in the sample. For instance, it is good practice after addition of a sample to the solution containing the immobilized antigen or antigen analogue, to account for any agglutination that may have been caused by the sample.

Exemplary latex polymers for use with this procedure include polystyrene latex particles having functional groups that can react with amino groups on their surface. Such functional groups include chlorosilyl; alkoxysilyl; activated carboxyl; chloromethylphenyl; epoxy groups; and Cl—$CY_2CH_2(CH_2)_q CY_2$NH—L—NH— groups, where $CY_2$ is methylene or keto. A particularly useful polymer is a polystyrene latex polymer having a polystyrene core, with a glycidyl methacrylate polymer or copolymer as a shell. Procainamide analogs of Formula 3 or 8 may be directly reacted with polystyrene/glycidyl methacrylate core/shell particles, binding the conjugates by reaction between the aliphatic amino group on the analogs and the reactive epoxide rings. Particles having styrene-butadiene latex cores and shells containing glycidyl methacrylate monomers or hydroxyalkyl methacrylate ester monomers are also suitable. The procainamide analogs of Formula 6 or 22 may be bound to styrene-butadiene/glycidyl methacrylate core/shell particles in a similar fashion. To bind the procainamide analogs to styrene-butadiene/glycidyl methacrylate core/shell particles, the particles may be reacted with N,N-disuccinimidyl carbonate, activating the exposed hydroxyl groups to $SN_2$ attack. The activated latex particles then are reacted with the procainamide analogs of Formula 6 or 22. Since steric repulsion between bound surface components plays a key role in stability of the conjugate particles, it is preferred to conduct the coupling reaction between the latex particle and the procainamide analog in the presence of a polyether polyamine linking agents, such as 1,8-diamino-3,6-dioxaoctane (DA-10). This diamine tends to bind to any unreacted glycidyl or activated hydroxyl groups on the surface of the latex particles, increasing the level of bound surface components on the particles without providing additional groups which will interact with the procainamide antibody. The result is increased steric interaction between groups on the particle surface, resulting in greater particle stability.

Upon addition of antibody to assay medium with analyte containing sample, competition for the antibody occurs between the free analyte and the particle-bound antigen. This competition results in an inhibition of the formation of insoluble complexes observed in the absence of analyte, and inhibits the increase in turbidity.

A description of a PETINIA based assay is as follows: A measure of absorbance r0 ($\lambda$=340-700 nm) in an empty sample cuvette is taken at time t0 (e.g., 0 sec.) and used as a control value. A known volume of a particle reagent having a defined concentration of particle/procainamide analog conjugate is added to the sample cuvette at time t1 (e.g., 16 sec.), resulting in a solution having a known volume v0. An increased absorbance occurs upon addition of particle reagent. Generally 340 nm is the wavelength of choice because the complex absorbs maximally at that wavelength.

At this point t2 (e.g., 66 sec.), a known volume of a sample solution suspected of containing procainamide is added to the sample cuvette, increasing the solution volume to a volume v1. Absorbance r1 at a wavelength of 340-700 nm is then recorded at a time t3 (e.g., 102 sec.), and a second absorbance r2 is recorded at a second, later, time t4 (e.g., 252 sec.). The absorbance at 700 nm is observed to subtract background noise. Certain other wavelengths as known to the skilled in the art may also be used. The difference between these values at 340 nm (r2−r1) provides a good measure of the presence of nonspecific binding between the sample and the particle reagent in the test solution; if this difference is greater than 50 mAU, the particle reagent may have agglutinated in the absence of antibody, and the results of the test may be unreliable.

A known quantity of antibody reagent is then added to the test solution at time t5 (e.g., 282 sec.), increasing the solution volume to a volume v3. The absorbance undergoes an initial decrease due to the increase in the solution volume; next, the absorbance undergoes a gradual increase as the antibody reacts with the antigen particles, resulting in a formation of insoluble complexes. Any free antigen in the sample solution will compete competitively with antigen particles for the available antibody, resulting in measurable inhibition of the increase in turbidity. Thus, the rate at which turbidity increases is dependent on the concentration of analyte present. At a later time, t6 (e.g., 438 sec.), absorbance r3 is measured. Note that the specific time values and wavelengths provided here are exemplary only; a person skilled in the art will recognize that different values may also be used with success.

This absorbance data may then be used to obtain information about the rate of particle agglutination. This rate is affected by competition for antibodies between the procainamide in solution and the particle-bound procainamide analog. This competition leads to a reduction in the rate of particle agglutination. Under the assumption that changes in the rate of particle agglutination are dependent on the concentration of free procainamide in solution, agglutination rates may be used to derive the concentration of free procainamide in solution. This rate data may be calculated using the following equation (Equation 1):

$$\text{Rate}=r3-((v1/v3)*r2)-((1-v1/v3)*r0) \qquad \text{(Equation 1)}$$

In the above equation, (v1/v3) is the ratio of the solution volume at the time absorbance measurement r1 is taken to the solution volume at the time absorbance measurement r3 is taken. By analyzing several known concentrations of procainamide in solution, a standard curve can be generated. From this curve, the rate calculated from the analysis of an unknown sample can then be directly translated into a procainamide concentration via some typical curve fitting algorithm, such as a Logit fit.

The following precautions should be taken in using this method. If the difference between r2 and r0 at 340 nm is greater than 1700 mAU, and/or the difference between r2 and r0 at 700 nm is greater than 100 mAU, the reaction solution in the cuvette may contain foam, causing the results to be of dubious value. If r1−r0<350 mAU, or if r2−r1>50 mAU, there may be particle agglutination in the absence of antibody (or non-specific agglutination). If the Final Optical Density (FOD) at 340 nm exceeds 1700 mAU, the absorbance of the solution is above the linear response region and possibly the detection limit of the analyzer. The results of the PETINIA assay may then have unacceptable linearity, and should be rejected.

Other examples of known immunoassay formats, which can be employed using the reporter reagents of the present invention, include direct agglutination particle-based immunoassays, enzyme-linked immunosorbent immunoassays, and fluorescence-based immunoassays.

SYNTHESIS EXAMPLE 2

Particle Reagent Preparation (A) Preparation of Polystyrene/Polyglycidyl Methacrylate Polymer Particle The polymer latex was an aqueous dispersion of polymer particles that consist of a core of poly(styrene) and a glycidyl methacrylate shell, prepared as described in Craig, U.S. Pat. No. 4,480,042.

(B) Conjugation of Procainamide to Polymer Particles

The procainamide-conjugated particle reagent was prepared using the following reagents:

a) A solution of procainamide analog 22 was prepared by dissolving 157 mg 22 in a mixture of DMSO and methanol to produce a solution which contained 34.9 mg/ml 22 (80.2 mM).

b) A solution of DA-10 (1,8-diamino-3,6-dioxaoctane) was prepared by dissolving 0.500 mL DA-10 in 10 mL water. Sufficient aqueous HCl was then added to bring the pH of the solution to 9.2. The final solution had a DA-10 concentration of 39.34 mg/mL (264 mM).

c) A wash buffer solution was prepared containing 0.464 g/L sodium phosphate monobasic; 1.65 g/L sodium phosphate dibasic; 62.5 mL/L of a 16% aqueous solution of the surfactant Gafac; 0.06 g/L of neomycin sulfate; and 2.0 mL/L of the broad spectrum antimicrobial Proclin 300. The pH of the solution was adjusted to 7.8 by titration with 5N NaOH.

A polystyrene/polyglycidyl methacrylate particle solution, was used to prepare the particle reagent solution. 5 mL of a particle solution having 10.3% solids was obtained. 0.243 mL of the solution of procainamide analog (80.2 mM stock solution), 0.10 mL of the DA-10 solution (324 mM stock solution), and 0.27 mL of a 14.7% aqueous solution of the surfactant Gafac were added dropwise with stirring to the polystyrene/polyglycidyl methacrylate particle solution. The resulting mixture contained concentrations of 3.50 mM procainamide analog 22; 3.00 mM DA-10; and 0.07 wt. % Gafac. The final solids content was 9.24%. The pH was measured, and adjusted to 9.2. The reaction mixture was then allowed to react at 70° C. for 18 hr. At the end of this time, 10 mL of a wash buffer solution [1.0% Gafac, 15 mM Phosphate, 0.2% Proclin 300 and 0.006% Neomycin Sulfate (pH 7.8)] was added to the reaction mixture, and the resulting mixture was subjected to centrifugation at 28,000 rpm. The liquid supernatent was decanted, and 20 mL wash buffer was added to the solid material. The solid material was resuspended in the wash buffer by sonication. The process of centrifugation and resuspension was repeated 3 more times. After the final centrifugation, the final solid pellet is taken up into sufficient wash buffer to have a final volume of 20 mL, and a final particle concentration of 50 mg/mL.

IMMUNOASSAY EXAMPLE 1

Use of Particle Reagent in PETINIA Assays for Procainamide

A. Calculation of Particle Agglutination Rates.

The procainamide-particle conjugates prepared as described above were diluted to a concentration of 2.0 mg/mL in the wash buffer solution to obtain a particle reagent (PR). Anti-procainamide monoclonal antibodies were diluted in antibody diluent to prepare an antibody reagent (AB). The antibody diluent had a pH of 6.5, and included 100 mM Phosphate, 1 M NaCl, 1% BSA, 0.2% Proclin 300 and 0.006% Neomycin Sulfate. The concentration of antibodies in the diluent was 75 µg/mL. An assay buffer having a pH of 7.7 comprising phosphate (100 mM); 0.3 wt. % Gafac; KCl (100 mM); 0.2 wt. % Proclin 300; and 0.006 wt. % neomycin sulfate was prepared.

The assay was carried out on a Dimension® Clinical Chemistry system from Dade Behring Inc, Deerfield, Ill., using a sample solution containing free procainamide. At time t=0 sec., the absorbance r0 of an empty cuvette at 340-700 nm was measured as a control air blank. At time t=16 sec., 80 µl PR and 130 µl of assay buffer followed by 103 µl of water were added to the cuvette. At time t=66 sec, 2 µl of sample followed by 32 µl of water were added to the cuvette. Later, at time t=102.9 sec., the absorbance r1 of the test solution was recorded at a total solution volume v1 of 347 µl. A second absorbance r2 was recorded at time t=254.4 sec. The difference between r2 and r1 was found to be less than 50 mAU; therefore, the risk of particle agglutination from excessive non-specific binding was deemed to be acceptable. Thus, at time t=284.8 sec., 80 µl of AR followed by 40 µl of water was added to the test solution. Finally, at time t=436.3 sec, the absorbance r3 of the test solution was recorded at a final solution volume v3 of 347 µl. The absorbance of the test solution as a function of time has been plotted in FIG. 1; and the numerical results of this experiment have been tabulated in Table 1. Using the numbers generated from the experiment described above, a measurement of the rate of particle agglutination can be derived from the above results, in accordance with equation 1. Using this expression, a Rate value of 176.0 mAU may be calculated.

TABLE 1

Absorbance as a Function of Time During a PETINIA Assay.

| Time (Sec.) | Volume (µL) | Absorbance (mAU) (340-700 nm) |
|---|---|---|
| 0 | 0 | 65.73 (r0) |
| 18.1 | 313 | 929.92 |
| 66.6 | 347 | 950.04 |
| 102.9 | 347 (v1) | 871.74 (r1) |
| 254.4 | 347 | 898.04 (r2) |
| 284.8 | 467 | 902.43 |
| 436.3 | 467 (v3) | 860.09 (r3) |

B. Determination of a Standard Curve For PETINIA Assays.

The procedure described above for determination of Rate values was applied to sample solutions having known procainamide concentrations of 0 µg/mL, 2.16 µg/mL, 4.33 µg/mL, 8.66 µg/mL, and 17.32 µg/mL. For each solution, values correlating to the rate of particle agglutination were calculated in accordance with Equation 1, and the calculated data was tabulated in Table 2. The rate data from Table 2 was fit to a logit curve in order to generate a standard curve, shown in FIG. 2.

TABLE 2

Rate of Agglutination as a Function of Free Procainamide Concentration.

| | [PROC], µg/mL | | | | |
|---|---|---|---|---|---|
| | 0 | 2.16 | 4.33 | 8.66 | 17.32 |
| Rate (mAU) | 224.07 | 178.86 | 129.70 | 55.47 | 24.21 |

C. Comparison of Results from PETINIA Assay and EMIT® Assay.

The effectiveness of the PETINIA assay as described above was verified by comparing the results of PETINIA assays to the commonly used EMIT® assay (Enzyme Multiplied Immunoassay). The EMIT® assay was performed on an aca® discrete clinical analyzer from Dade Behring Inc., Deerfield, Ill, using purified water and an aca® analyzer PROC Analytical Test Pack. The analyzer performed the test steps automatically at a temperature of 37° C. In brief, a 40 µL sample of human serum was diluted with purified water by the analyzer. Tablets containing 500 µmol of TRIS buffer and 0.9 mmol of NaCl from the Analytical Test Pack were added to the test solution. Then, 66 µL of a solution of sheep-derived procainamide antibody was added to the sample solution from the Analytical Test Pack by the analyzer. 66 µL of a solution of procainamide/glucose-6-phosphate dehydrogenase conjugate was next added to the sample solution, and allowed to complex to any antibody that had not already complexed to procainamide in the original serum sample. Next, a tablet containing the enzyme substrate glucose-6-phosphate (75 µmol) and NAD⁺ (65 µmol), and allowed to react with any non-complexed conjugate, forming NADH and 6-phosphogluconolactone. The analyzer monitors the change in absorbance at 340 nm to determine the increase in NADH concentration, and derives the original procainamide concentration from this value.

A number of samples believed to contain procainamide were then tested by the above-described EMIT® method, and the data are recorded in Table 4. The same set of samples was then retested, using the PETINIA assay technique described in Example 1 and recorded in Table 4. To determine how well the values derived from the two methods correlate, the concentrations from the EMIT® data from the aca® analyzer were plotted against the concentrations from the PETINIA data (FIG. 3). The result was a straight line having a slope of 1.03, and a y-intercept of 0.64. The R squared value was 0.9944, the ideal value of 1.00. These results demonstrate that the two methods produce results that correlate well.

TABLE 4

Comparison of Results from a PETINIA Assay to Results from an EMIT ® Assay.

| | PETINIA | | EMIT ® |
|---|---|---|---|
| Sample # | Absorbance (mAU) | Analyte Concentration (µg/mL) | Analyte Concentration (µg/mL) |
| #1 | 162.42 | 2.91 | 2.5 |
| #2 | 147.62 | 3.49 | 2.7 |
| #3 | 128.27 | 4.28 | 3.4 |

TABLE 4-continued

Comparison of Results from a PETINIA Assay to Results from an EMIT ® Assay.

| | PETINIA | | EMIT ® |
| --- | --- | --- | --- |
| Sample # | Absorbance (mAU) | Analyte Concentration (µg/mL) | Analyte Concentration (µg/mL) |
| #4 | 111.37 | 5.04 | 4.4 |
| #5 | 139.05 | 3.84 | 2.9 |
| #6 | 155.12 | 3.20 | 2.5 |
| #7 | 104.70 | 5.36 | 4.3 |
| #8 | 72.08 | 7.34 | 6.4 |
| #9 | 21.85 | 18.72 | 17.5 |
| #10 | 137.68 | 3.89 | 3.2 |
| #11 | 178.52 | 2.27 | 1.5 |
| #12 | 168.48 | 2.67 | 1.8 |
| #13 | 90.00 | 6.15 | 5.6 |
| #14 | 124.84 | 4.43 | 3.9 |
| #15 | 125.49 | 4.40 | 3.7 |
| #16 | 213.76 | 0.62 | 0.1 |
| #17 | 113.33 | 4.95 | 4.5 |
| #18 | 71.86 | 7.36 | 6.4 |
| #19 | 119.70 | 4.66 | 3.8 |
| #20 | 181.74 | 2.14 | 1.2 |
| #21 | 196.76 | 1.49 | 0.5 |
| #22 | 97.98 | 5.71 | 4.6 |
| #23 | 112.47 | 4.99 | 3.8 |
| #24 | 142.48 | 3.70 | 2.9 |
| #25 | 183.94 | 2.05 | 1.2 |
| #26 | 119.52 | 4.66 | 3.8 |
| #27 | 101.07 | 5.54 | 4.9 |
| #28 | 161.68 | 2.94 | 1.9 |
| #29 | 117.39 | 4.76 | 3.5 |
| #30 | 176.48 | 2.35 | 1.6 |
| #31 | 135.20 | 3.99 | 3.4 |
| #32 | 102.65 | 5.46 | 4.9 |
| #33 | 138.55 | 3.86 | 2.9 |
| #34 | 54.42 | 8.98 | 7.9 |
| #35 | 54.02 | 9.03 | 7.8 |
| #36 | 115.75 | 4.83 | 4.7 |
| #37 | 65.98 | 7.84 | 7.2 |
| #38 | 32.91 | 12.83 | 11.7 |
| #39 | 31.51 | 13.26 | 11.9 |
| #40 | 48.11 | 9.78 | 8.7 |
| #41 | 90.37 | 6.13 | 5.6 |
| #42 | 34.35 | 12.42 | 10.6 |
| #43 | 54.30 | 8.99 | 8.3 |
| #44 | 118.75 | 4.70 | 4.1 |
| #45 | 76.30 | 7.03 | 6.5 |
| #46 | 32.40 | 12.98 | 11.9 |
| #47 | 41.84 | 10.78 | 9.8 |
| #48 | 61.98 | 8.20 | 7.6 |
| #49 | 90.07 | 6.15 | 5.8 |
| #50 | 32.78 | 12.86 | 11.8 |
| #51 | 99.77 | 5.61 | 5.1 |
| #52 | 47.26 | 9.90 | 8.9 |
| #53 | 64.81 | 7.94 | 7.3 |

Although the present invention has been described in detail with particular reference to preferred embodiments thereof, it should be understood that the invention is capable of other different embodiments, and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only, and do not in any way limit the invention, which is defined only by the claims.

What is claimed is:

1. A latex polymer-bound procainamide analog, having a structure represented by of:

a compound of Formula 7:

$$(NH_2)_n\text{-}C_6H_4\text{-}C(O)\text{-}NH\text{-}CH_2CH_2\text{-}N(CY_2\text{-}CHR\text{-}CY_2)\text{-}(CH_2)_q\text{-}NH\text{-}L\text{-}NH\text{-}Polymer$$

Formula 7 wherein:

R is hydrogen or alkyl;

each $CY_2$ group is a carbonyl group;

L is a linking group selected from the group consisting of $(CH_2)_m$ and $(CH_2CH_2O)_pCH_2CH_2$, where m is between 2 and 10 and p is between 1 and 4;

polymer is a polymer having functional groups that react with aliphatic amino groups;

n is 1; and q is between 2 and 10.

2. The latex polymer-bound procainamide analog of claim 1, wherein the polymer is in the form of particles.

* * * * *

UNITED STATES PATENT AND TRADEMARK OFFICE
CERTIFICATE OF CORRECTION

PATENT NO.         : 7,279,340 B2                                        Page 1 of 1
APPLICATION NO. : 10/819831
DATED              : October 9, 2007
INVENTOR(S)        : Chu et al.

It is certified that error appears in the above-identified patent and that said Letters Patent is hereby corrected as shown below:

On Title page, Item (75), line 9, please delete "Neward" and insert --Newark--

Signed and Sealed this

Thirtieth Day of September, 2008

JON W. DUDAS
*Director of the United States Patent and Trademark Office*